United States Patent
Lin et al.

(10) Patent No.: US 9,274,089 B2
(45) Date of Patent: Mar. 1, 2016

(54) APPARATUS AND A METHOD FOR MEASURING IN-PLANE ELASTIC CONSTANTS FOR A LAMINATE

(71) Applicant: The Boeing Company, Chicago, IL (US)

(72) Inventors: John Z Lin, Renton, WA (US); Richard H Bossi, Renton, WA (US)

(73) Assignee: The Boeing Company, Chicago, IL (US)

( * ) Notice: Subject to any disclaimer, the term of this patent is extended or adjusted under 35 U.S.C. 154(b) by 676 days.

(21) Appl. No.: 13/665,019

(22) Filed: Oct. 31, 2012

(65) Prior Publication Data

US 2014/0122000 A1    May 1, 2014

(51) Int. Cl.
| | | |
|---|---|---|
| *G01H 5/00* | (2006.01) | |
| *G01D 21/00* | (2006.01) | |
| *G06F 17/40* | (2006.01) | |
| *G06F 19/00* | (2011.01) | |
| *G01N 29/07* | (2006.01) | |
| *G01N 29/24* | (2006.01) | |

(52) U.S. Cl.
CPC .................. *G01N 29/07* (2013.01); *G01H 5/00* (2013.01); *G01N 29/2418* (2013.01); *G01D 21/00* (2013.01); *G01N 2291/0231* (2013.01); *G01N 2291/02827* (2013.01); *G01N 2291/2694* (2013.01); *G06F 17/40* (2013.01); *G06F 19/00* (2013.01)

(58) Field of Classification Search
None
See application file for complete search history.

(56) References Cited

U.S. PATENT DOCUMENTS

| | | | | |
|---|---|---|---|---|
| 3,690,155 A | * | 9/1972 | Eichler | G01N 29/07 73/597 |
| 5,127,268 A | * | 7/1992 | Kline | G01N 29/07 73/597 |
| 5,361,638 A | * | 11/1994 | Pettersson | G01N 3/317 356/429 |

(Continued)

FOREIGN PATENT DOCUMENTS

| | | |
|---|---|---|
| DE | 10 2008 021248 A1 | 11/2009 |
| WO | WO89/06796 A1 | 7/1989 |

OTHER PUBLICATIONS http://en.wikiversity.org/wiki/Introduction_to_Elasticity/Constitutive_relations dated Oct. 31, 2012, 6 pgs.

(Continued)

*Primary Examiner* — Edward Cosimano
(74) *Attorney, Agent, or Firm* — Womble Carlyle Sandridge & Rice LLP

(57) ABSTRACT

An apparatus is provided that includes a wave generator, plurality of transducers and processing device. The wave generator may be configured to simultaneously generate a plurality of acoustic waves that propagate through a laminate along a plurality of in-plane directions. The transducers may be spaced apart from one another and positionable at one or more known distances from the wave generator along respective in-plane directions. The transducers may be configured to detect acoustic waves propagating through the laminate along the respective in-plane directions. The processing device may be coupled to the transducers and configured to simultaneously calculate a plurality of elastic constants of the laminate as a function of velocities of the acoustic waves detected by the transducers. And the processing device may be configured to calculate the velocities as a function of the known distance(s) and arrival times of the acoustic waves at the transducers.

20 Claims, 3 Drawing Sheets

(56) References Cited

U.S. PATENT DOCUMENTS

| | | | |
|---|---|---|---|
| 5,408,882 A | 4/1995 | McKinley et al. | |
| 5,748,318 A * | 5/1998 | Maris | G01N 21/1702 356/630 |
| 5,959,735 A * | 9/1999 | Maris | G01N 21/1702 250/201.2 |
| 6,175,416 B1 * | 1/2001 | Maris | G01N 21/1702 356/432 |
| 6,208,421 B1 * | 3/2001 | Maris | G01N 21/1702 356/432 |
| 6,271,921 B1 * | 8/2001 | Maris | G01N 21/1702 356/432 |
| 6,363,787 B1 * | 4/2002 | Carlson | G01B 17/025 73/579 |
| 6,400,449 B2 * | 6/2002 | Maris | G01N 21/1702 356/128 |
| 6,920,790 B2 | 7/2005 | Huang et al. | |
| 6,941,231 B2 * | 9/2005 | Zeroug | G01N 29/07 702/39 |
| 7,603,904 B2 * | 10/2009 | Harris et al. | 73/597 |
| 2001/0028460 A1 * | 10/2001 | Maris | G01N 21/1702 356/432 |
| 2004/0054474 A1 * | 3/2004 | Zeroug | G01N 29/07 702/1 |
| 2006/0185439 A1 * | 8/2006 | Harris et al. | 73/760 |

OTHER PUBLICATIONS

European Search Report dated Jul. 15, 2014 for European Application No. 13 189 947.8, 5 pages.

\* cited by examiner

APPARATUS AND A METHOD FOR MEASURING IN-PLANE ELASTIC CONSTANTS FOR A LAMINATE

TECHNOLOGICAL FIELD

The present disclosure relates generally to nondestructive testing and, in particular, to determining one or more in-plane elastic constants for a laminate plate or plate-like structure.

BACKGROUND

In a variety of mechanical or structural devices or assemblies including, for example, aircraft, spacecraft and other types of vehicles or vessels; buildings; bridges and other structures, it is frequently desired to be able to determine material properties or changes in material properties of a given part. The design and safe operation of a part depends on having particular properties at particular orientations or locations in the part. Further, any changes in material properties may be indicative of degradation of the part. For example, material stiffness may be an important parameter affecting the performance of a structure. While structures may be designed based on a known initial stiffness of the materials making up the structure, various factors may cause the materials to lose stiffness.

Stress, fatigue and environmental attack such as thermal and/or oxidation processes are just a few of the mechanisms by which a material may be degraded in terms of material stiffness. Fiber/matrix composite materials may be particularly susceptible to stiffness degradation, chiefly through a process known as micro-cracking in which microscopic cracks may develop in the matrix material that binds the fibers together. Such micro-cracking may cause deleterious changes in mechanical properties, stress concentration, and redistribution within the composite material, which in turn may lead to performance degradation, delamination, and fiber damage.

It may be important to quantitatively determine material properties of a plate such as a composite laminate plate along an in-plane direction of the plate, such as to determine its condition at manufacture and/or in-service.

Therefore, it may be desirable to have an apparatus and method that takes into account at least some of the issues discussed above, as well as possibly other issues.

BRIEF SUMMARY

Example implementations of the present disclosure are generally directed to an apparatus and method for measuring in-plane elastic constants of a generally orthotropic monolithic or composite laminate such as a continuous fiber reinforced composite lamina or thin laminate. The apparatus and method of one example may use a laser-generated ultrasound source and a single sample, and may involve the measurements of in-plane longitudinal and transverse wave velocities in three directions simultaneously. The measured in-plane velocities may in turn be algorithmically related to one or more elastic constants such as Young's modulus, Poisson's ratio and shear modulus in two orthogonal directions. Example implementations of the present disclosure may provide a rapid and cost-effective means to obtain elastic properties of generally-orthotropic composites and enables in-situ monitoring of material degradation in composite structures.

According to one aspect of example implementations, the apparatus includes a wave generator, plurality of transducers and processing device. The wave generator may be configured to simultaneously generate a plurality of acoustic waves that propagate through a laminate along a plurality of in-plane directions. In one example, the wave generator may include a target inducible to generate ultrasonic waves by an energy source configured to direct a pulse onto the target. In one example, the energy source may be an ultrasonic transducer.

The transducers may be spaced apart from one another and positionable at one or more known distances from the wave generator along respective in-plane directions. In various examples, the transducers may be positionable an equal, known distance r from the wave generator, or one or more of the transducers may be positionable at different, known distances. In either instance, the transducers may be positionable along respective ones of 0°, 45° and 90° in-plane directions. The transducers may be configured to detect acoustic waves propagating through the laminate along the respective in-plane directions. Additionally or alternatively, for example, the apparatus may include a support arm to which the transducers are affixed spaced apart from one another. In this example, the support arm may be positionable to thereby position the transducers along respective ones of the 0°, 45° and 90° in-plane directions.

The processing device may be coupled to the transducers and configured to simultaneously calculate a plurality of elastic constants of the laminate as a function of velocities of the acoustic waves detected by the transducers. The processing device may be configured to calculate the velocities as a function of the known distance(s) and arrival times of the acoustic waves at the transducers. In one example, the in-plane directions include orthogonal first and second in-plane directions. In this example, the processing device being configured to simultaneously calculate the plurality of elastic constants may include being configured to calculate Young's moduli, Poisson's ratios and shear modulus in the orthogonal first and second in-plane directions.

In an even more specific example in which the transducers may be positionable along respective ones of 0°, 45° and 90° in-plane directions, the velocities of the acoustic waves detected by the transducers may include longitudinal wave velocities in the 0°, 45° and 90° in-plane directions, and a transverse wave velocity in the 0° in-plane direction. In this example, the processing device may be configured to simultaneously calculate the Young's moduli, Poisson's ratios and shear modulus based on the longitudinal wave velocities in the 0°, 45° and 90° in-plane directions, the transverse wave velocity in the 0° in-plane direction, and a known density of the laminate.

In other aspects of example implementations, a processing device and method are provided for measuring in-plane elastic constants for a laminate. The features, functions and advantages discussed herein may be achieved independently in various example implementations or may be combined in yet other example implementations further details of which may be seen with reference to the following description and drawings.

BRIEF DESCRIPTION OF THE DRAWING(S)

Having thus described example implementations of the disclosure in general terms, reference will now be made to the accompanying drawings, which are not necessarily drawn to scale, and wherein:

DETAILED DESCRIPTION

Figure 1:
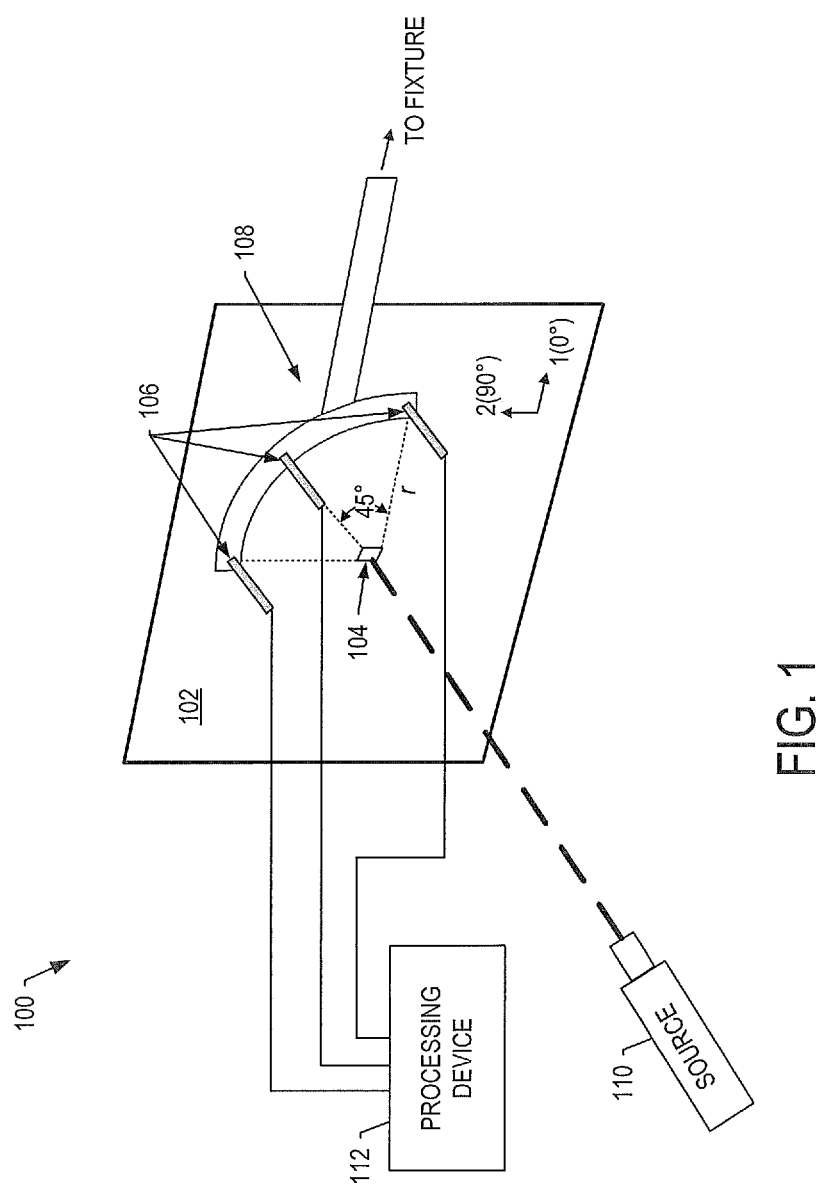
FIG. 1 illustrates an apparatus according to one example implementation.

Some implementations of the present disclosure will now be described more fully hereinafter with reference to the accompanying drawings, in which some, but not all implementations of the disclosure are shown. Indeed, various implementations of the disclosure may be embodied in many different forms and should not be construed as limited to the implementations set forth herein; rather, these example implementations are provided so that this disclosure will be thorough and complete, and will fully convey the scope of the disclosure to those skilled in the art. Like reference numerals refer to like elements throughout.

The general state of stress at a point on a composite laminate plate may be represented by normal stresses in three directions, as well as shear stresses on three planes. The normal stresses may include $\sigma_{11}$ representing normal stress along the 0° (fiber) in-plane material principal direction (e.g., x-direction), $\sigma_{22}$ representing normal stress along the orthogonal 90° in-plane material principal direction (e.g., y-direction), and $\sigma_{33}$ representing normal stress in the thickness direction (e.g., z-direction). In the preceding, subscripts 1 and 2 may represent the two in-plane material principal directions, and subscript 3 may represent the thickness direction, normal to the 1-2 plane. The shear stresses, then, may include $\sigma_{23}$ representing shear stress on the 2-3 plane, $\sigma_{31}$ representing stress on the 3-1 plane, and $\sigma_{12}$ representing shear stress on the 1-2 plane.

Each stress $\sigma_{11}$, $\sigma_{22}$, $\sigma_{33}$, $\sigma_{23}$, $\sigma_{31}$ and $\sigma_{12}$ may produce a respective strain $\epsilon_{11}$, $\epsilon_{22}$, $\epsilon_{33}$, $\epsilon_{23}$, $\epsilon_{31}$ and $\epsilon_{12}$. For a generally orthotropic solid and in the material principal coordinate system, the elastic stress-strain relationship may be written as:

$$\begin{Bmatrix} \sigma_{11} \\ \sigma_{22} \\ \sigma_{33} \\ \sigma_{23} \\ \sigma_{31} \\ \sigma_{12} \end{Bmatrix} = \begin{bmatrix} C_{11} & C_{12} & C_{13} & 0 & 0 & 0 \\ C_{12} & C_{22} & C_{23} & 0 & 0 & 0 \\ C_{13} & C_{23} & C_{33} & 0 & 0 & 0 \\ 0 & 0 & 0 & C_{44} & 0 & 0 \\ 0 & 0 & 0 & 0 & C_{55} & 0 \\ 0 & 0 & 0 & 0 & 0 & C_{66} \end{bmatrix} \begin{Bmatrix} \epsilon_{11} \\ \epsilon_{22} \\ \epsilon_{33} \\ 2\epsilon_{23} \\ 2\epsilon_{31} \\ 2\epsilon_{12} \end{Bmatrix} \quad (1)$$

In equation (1), C represents the stiffness tensor, which includes a number of component constants ($C_{11}$, $C_{22}$, $C_{33}$, $C_{12}$, $C_{13}$, $C_{23}$, $C_{44}$, $C_{55}$, $C_{66}$).

It can be shown by solving the Christoffel equations that the phase velocities of longitudinal and the transverse waves $V_L(\theta)$, $V_T(\theta)$ (both polarized in the 1-2 plane for any angle $\theta$) may be given by:

$$2\rho V_L^2(\theta) = A + \sqrt{A^2 - 4C} \quad (2)$$

$$2\rho V_T^2(\theta) = A - \sqrt{A^2 - 4C} \quad (3)$$

In equations (2) and (3), $\rho$ represents the plate density, and A represents in-plane stiffness. And from the foregoing, C and A may be represented as follows:

$$A = C_{66} + C_{11} \cos^2(\theta) + C_{22} \sin^2(\theta) \quad (4)$$

$$C = [C_{11} \cos^2(\theta) + C_{66} \sin^2(\theta)][C_{66} \cos^2(\theta) + C_{22} \sin^2(\theta)] - (C_{12} + C_{66})^2 \cos^2(\theta) \sin^2(\theta) \quad (5)$$

Setting $\theta = 0°$, 45° and 90° in equations (4) and (5), one may arrive at the following four independent equations for solving four unknown in-plane constants $C_{11}$, $C_{22}$, $C_{12}$ and $C_{66}$:

$$2\rho V_L^2(0) = C_{11} \quad (6)$$

$$2\rho V_T^2(0) = C_{66} \quad (7)$$

$$2\rho V_L^2(90) = C_{22} \quad (8)$$

$$2\rho V_L^2(45) = \left(C_{66} + \frac{C_{22} + C_{11}}{2}\right) + \sqrt{\left(\frac{C_{11} - C_{22}}{2}\right)^2 + (C_{11} + C_{66})^2} \quad (9)$$

Assuming plane stress condition for in-plane waves described above, which may be considered approximately accurate for a thin composite lamina or laminate and traction free boundary conditions in the 3-direction, four in-plane stiffness constants may be further reduced to:

$$C_{11} = \frac{E_1}{1 - \upsilon_{21}\upsilon_{12}} \quad (10)$$

$$C_{22} = \frac{E_2}{1 - \upsilon_{21}\upsilon_{12}} \quad (11)$$

$$C_{12} = \frac{\upsilon_{21} E_2}{1 - \upsilon_{21}\upsilon_{12}} \quad (12)$$

$$C_{66} = G_{12} \quad (13)$$

In the preceding equations (10)-(13), $E_1$, $E_2$, $\upsilon_{12}$, $\upsilon_{21}$ and $G_{12}$ may be engineering elastic constants representing the in-plane Young's moduli ($E_1$, $E_2$), Poisson's ratios ($\upsilon_{12}$, $\upsilon_{21}$) and shear modulus ($G_{12}$) in the material principal directions.

From equations (6)-(13), the following explicit expression for engineering elastic constants may be derived:

$$\upsilon_{21} = \sqrt{\left(2R_L(45) - R_{TL}(0) - \frac{1 + R_L(90)}{2}\right)^2 - \left(\frac{1 - R_L(90)}{2}\right)^2 - R_{TL}(0)} \quad (14)$$

The variables in equation (14) may in turn be represented as follows:

$$R_L(45) = \frac{V_L^2(45)}{V_L^2(0)} \quad (14\text{-a})$$

$$R_{TL}(0) = \frac{V_T^2(0)}{V_L^2(0)} \quad (14\text{-b})$$

$$R_L(90) = \frac{V_L^2(90)}{V_L^2(0)} \quad (14\text{-c})$$

$$\upsilon_{12} = \frac{\upsilon_{21}}{R_L(90)} \quad (15)$$

$$E_1 = \rho V_L^2(0)(1 - \upsilon_{21}\upsilon_{12}) \quad (16)$$

$$E_2 = \rho V_L^2(90)(1 - \upsilon_{21}\upsilon_{12}) \quad (17)$$

$$G_{12} = \rho V_T^2(0) \quad (18)$$

The plate density $\rho$ may be known. Equations (14)-(18) (including equations 14-a, 14b, 14-c) therefore represent a set of eight simultaneous equations having nine unknowns, namely, $E_1$, $E_2$, $\upsilon_{12}$, $\upsilon_{21}$, $G_{12}$, $V_L(0)$, $V_L(90)$, $V_L(45)$ and $V_T(0)$. In accordance with example implementations of the present disclosure, the longitudinal and transverse wave velocities $V_L(0)$, $V_L(90)$, $V_L(45)$ and $V_T(0)$ may be determined, which may in turn enable determination of the in-plane Young's moduli ($E_1$, $E_2$), Poisson's ratios ($\upsilon_{12}$, $\upsilon_{21}$) and shear modulus ($G_{12}$) according to equations (14)-(18).

The longitudinal wave velocities $V_L$ in the $\theta=0°$, 45° and 90° directions, and transverse wave velocity $V_T$ in the $\theta=0°$ direction, may be experimentally determined by causing a wave to propagate along the plate and measuring the time of flight $t_{arrival}$ required for the wave to travel a known distance (e.g., distance r) along the plate in the respective directions, as explained in greater detail below. Example implementations of the present disclosure may be described primarily in the context of thin plates in which the thickness of the plate is much smaller than the length and width dimensions of the plate. It should be understood, however, that qualitative results may be obtained even for non-plate structures using the same or a similar methodology as that described herein. It is anticipated that quantitative results may even be obtained for non-plate structures by using empirically derived correction factors.

FIG. 1 illustrates various components of an apparatus 100 for measuring in-plane elastic constants of a generally orthotropic monolithic or composite laminate 102 such as a continuous fiber reinforced composite lamina or thin laminate. The apparatus and method of example implementations of the present disclosure may be utilized to determine changes in the material properties of a variety of mechanical or structural devices or assemblies. For example, the testing apparatus and method may be utilized to determine changes in the material properties of the composite laminate plate(s) that form the skin or other portions of the structural assembly of an aircraft. Similarly, for example, the apparatus and method may be employed to inspect the skin or other portions of the structural assembly of a spacecraft, a marine vessel, an automobile or other vehicle or vessel. In yet other examples, the apparatus and method may be employed to inspect other structures such as buildings, bridges or the like.

In accordance with one example implementation of the present disclosure, the apparatus 100 may include an acoustical wave generator 104 and a plurality of pin transducers 106 disposable against a major surface of the laminate 102 so as to be in acoustical communication with the laminate. In various examples, the wave generator may be permanently or removably fixed to or embedded in the laminate. In various examples, the transducers may be held against the laminate by a support arm 108 to which the transducers may be affixed. In one example, the support arm may be further secured to a fixture or other structure configured to hold the support arm and in turn the transducers in a fixed position against the laminate.

The acoustical wave generator 104 may be configured to generate in-plane acoustic (e.g., ultrasound) waves in a plurality of directions. The wave generator may be configured to generate the waves in a number of different manners. In one example, the wave generator may be a target such as aluminum tape that may be inducible to generate ultrasonic waves by an energy source 110 configured to direct a pulse onto the target. The energy source may be any of a number of suitable sources including laser sources, piezoelectric sources, transducers (e.g., ultrasonic transducer) or the like. And in various examples, as appropriate, a beam shaping lens or other element may be positioned between the source and target.

The transducers 106 may be configured to detect waves generated by the acoustical wave generator 104 in respective directions, and convert the acoustic waves into electrical waveforms. The transducers may be any of a number of suitable transducers including ultrasonic transducers, laser interferometers or the like. The transducers may be affixed to the support arm 108 spaced apart from one another and equidistant from the wave generator in respective directions. As shown, for example, the transducers may be affixed to the support arm spaced apart such that the transducers may be positioned an equal distance r from the wave generator. In another example, one or more (or even all) of the transducers may be positionable at different distances from the wave generator. The distance(s) may be selected in a number of different manners, such as in the range 6-15 cm. Regardless of whether the distance is the same or different for the transducers, the transducers may be positioned along respective ones of the 0°, 45° and 90° in-plane directions. In one example, the support arm may include a circular or otherwise curved portion to which the transducers may be affixed.

In non-isotropic configurations, the modulus/stiffness (and therefore the velocity) may be intentionally, directionally dependent. The waveform longitudinal and shear components may be separated in time be their velocity, and in magnitude by their interaction with the transducer, such that they may be independently measured by a transducer 106.

The transducers 106 and energy source 110 may be coupled to a suitable processing device 112, such as via wire or wireless connection. The processing device may be configured to control the generation of in-plane acoustic (e.g., ultrasound) waves by the acoustical wave generator 104. Similarly, the processing device may be configured to receive electrical waveforms from the transducers. The processing device may record the waveforms from respective transducers and determine the respective arrival times of the waves.

The distance(s) between the wave generator and transducers 106 may be known; and accordingly, the processing device 112 may be configured to determine wave velocities by dividing the known distance(s) by the arrival times. In this regard, the wave velocities may be determined in the $\theta=0°$, 45° and 90° directions along which the transducers are positioned, which may correspond to $V_L(0)$, $V_L(90)$, $V_L(45)$ and $V_T(0)$. The processing device, then, may be configured to calculate the in-plane Young's moduli ($E_1$, $E_2$), Poisson's ratios ($\upsilon_{12}$, $\upsilon_{21}$) and shear modulus ($G_{12}$) according to equations (14)-(18), as explained above.

According to example implementations of the present disclosure, the processing device 112 may be implemented by various means, which may include hardware, alone or under direction of one or more computer program code instructions, program instructions or executable computer-readable program code instructions from a computer-readable storage medium. In one example, one or more processing devices may be provided that are configured to function as or otherwise implement the processing device. In examples involving more than one processing device, the respective devices may be connected to or otherwise in communication with one another in a number of different manners, such as directly or indirectly via a wire or wirelessly.

Generally, one suitable processing device of example implementations of the present disclosure may comprise, include or be embodied in one or more fixed or portable electronic devices. Examples of suitable electronic devices include a smartphone, tablet computer, laptop computer, desktop computer, workstation computer, server computer or the like. The processing device may include one or more of each of a number of components such as, for example, a processor connected to a memory.

The processor is generally any piece of hardware that is capable of processing information such as, for example, data, computer-readable program code, instructions or the like (generally "computer programs," e.g., software, firmware, etc.), and/or other suitable electronic information. More particularly, for example, the processor may be configured to execute computer programs, which may be stored onboard the processor or otherwise stored in the memory (of the same or another processing device). The processor may be a number of processors, a multi-processor core or some other type of processor, depending on the particular implementation. Further, the processor may be implemented using a number of heterogeneous processor apparatuses in which a main processor is present with one or more secondary processors on a single chip. As another illustrative example, the processor may be a symmetric multi-processor apparatus containing multiple processors of the same type. In yet another example, the processor may be embodied as or otherwise include one or more application-specific integrated circuits (ASICs), field-programmable gate arrays (FPGAs) or the like. Thus, although the processor may be capable of executing a computer program to perform one or more functions, the processor of various examples may be capable of performing one or more functions without the aid of a computer program.

The memory is generally any piece of hardware that is capable of storing information such as, for example, data, computer programs and/or other suitable information either on a temporary basis and/or a permanent basis. In one example, the memory may be configured to store various information in one or more databases. The memory may include volatile and/or non-volatile memory, and may be fixed or removable. Examples of suitable memory include random access memory (RAM), read-only memory (ROM), a hard drive, a flash memory, a thumb drive, a removable computer diskette, an optical disk, a magnetic tape or some combination of the above. Optical disks may include compact disk-read only memory (CD-ROM), compact disk-read/write (CD-R/W), DVD or the like. In various instances, the memory may be referred to as a computer-readable storage medium which, as a non-transitory device capable of storing information, may be distinguishable from computer-readable transmission media such as electronic transitory signals capable of carrying information from one location to another. Computer-readable medium as described herein may generally refer to a computer-readable storage medium or computer-readable transmission medium.

In addition to the memory, the processor may also but need not be connected to one or more interfaces for displaying, transmitting and/or receiving information. The interfaces may include one or more communications interfaces and/or one or more user interfaces. The communications interface may be configured to transmit and/or receive information, such as to and/or from other processing device(s), network(s) or the like. The communications interface may be configured to transmit and/or receive information by physical (by wire) and/or wireless communications links. Examples of suitable communication interfaces include a network interface controller (NIC), wireless NIC (WNIC) or the like.

The user interfaces may include a display and/or one or more user input interfaces. The display may be configured to present or otherwise display information to a user, suitable examples of which include a liquid crystal display (LCD), light-emitting diode display (LED), plasma display panel (PDP) or the like. The user input interfaces may be by wire or wireless, and may be configured to receive information from a user into the processing device, such as for processing, storage and/or display. Suitable examples of user input interfaces include a microphone, image or video capture device, keyboard or keypad, joystick, touch-sensitive surface (separate from or integrated into a touchscreen), biometric sensor or the like. The user interfaces may further include one or more interfaces for communicating with peripherals such as printers, scanners or the like.

As indicated above, program code instructions may be stored in memory, and executed by a processor, to implement functions of the processing device described herein. As will be appreciated, any suitable program code instructions may be loaded onto a computer or other programmable apparatus from a computer-readable storage medium to produce a particular machine, such that the particular machine becomes a means for implementing the functions specified herein. These program code instructions may also be stored in a computer-readable storage medium that can direct a computer, a processor or other programmable apparatus to function in a particular manner to thereby generate a particular machine or particular article of manufacture. The instructions stored in the computer-readable storage medium may produce an article of manufacture, where the article of manufacture becomes a means for implementing functions described herein. The program code instructions may be retrieved from a computer-readable storage medium and loaded into a computer, processor or other programmable apparatus to configure the computer, processor or other programmable apparatus to execute operations to be performed on or by the computer, processor or other programmable apparatus.

Retrieval, loading and execution of the program code instructions may be performed sequentially such that one instruction is retrieved, loaded and executed at a time. In some example implementations, retrieval, loading and/or execution may be performed in parallel such that multiple instructions are retrieved, loaded, and/or executed together. Execution of the program code instructions may produce a computer-implemented process such that the instructions executed by the computer, processor or other programmable apparatus provide operations for implementing functions described herein.

Execution of instructions by a processor, or storage of instructions in a computer-readable storage medium, supports combinations of operations for performing the specified functions. It will also be understood that one or more functions, and combinations of functions, may be implemented by special purpose hardware-based computer systems and/or processors which perform the specified functions, or combinations of special purpose hardware and program code instructions.

Figure 2:
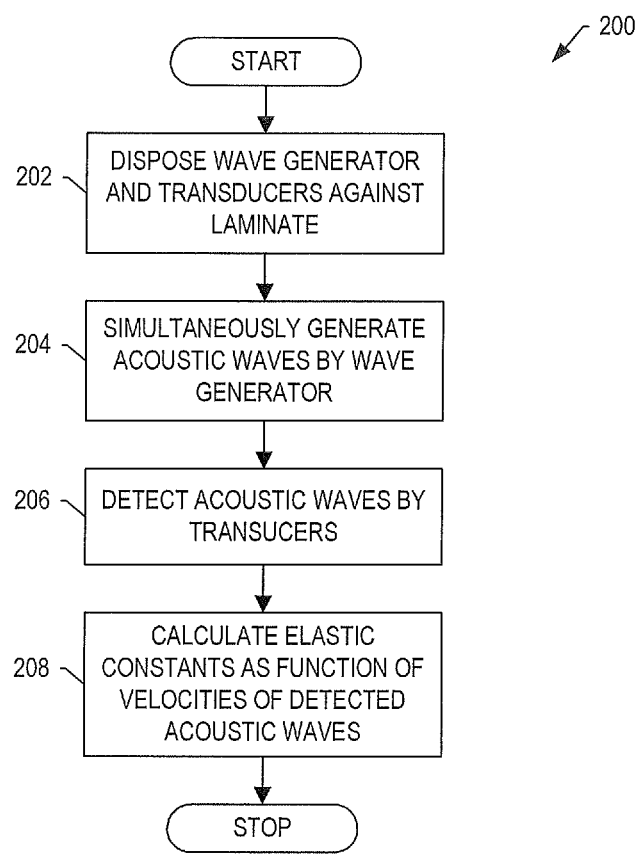
FIG. 2 is a flowchart illustrating various operations in a method according to various example implementations.

FIG. 2 illustrates various operations in a method 200 according to example implementations of the present disclosure. The method may include disposing a wave generator 104 and plurality of transducers 106 against a major surface of a laminate 102, as shown in block 202. The wave generator and transducers may be disposed so as to be in acoustical communication with the laminate. And in one example, the wave generator and transducers may be disposed against a portion of an aircraft that includes the laminate.

As shown in block 204, the method may include the wave generator 104 simultaneously generating a plurality of acoustic waves that propagate through a laminate 102 along a plurality of in-plane directions. In one example, the wave generator may include a target, and an energy source may direct a pulse onto the target to thereby induce the target to generate ultrasonic waves.

As shown in block 206, the method may also include the transducers 106 detecting acoustic waves propagating through the laminate along the respective in-plane directions.

The transducers 106 may be spaced apart from one another and positioned one or more known distances from the wave generator along respective in-plane directions. In various examples, the transducers may be positioned an equal, known distance r from the wave generator, or one or more of the transducers may be positioned at different, known distances. In either instance, the transducers may be positioned along respective ones of 0°, 45° and 90° in-plane directions. Additionally or alternatively, for example, the apparatus may include a support arm to which the transducers are affixed spaced apart from one another. In this example, the support arm may be positioned to thereby position the transducers along respective ones of the 0°, 45° and 90° in-plane directions.

As shown in block 208, the method may also include the processing device 112 simultaneously calculating a plurality of elastic constants of the laminate as a function of velocities of the acoustic waves detected by the transducers, with the velocities being calculated as a function of the distance(s) and arrival times of the acoustic waves at the transducers. In one example, the in-plane directions include orthogonal first and second in-plane directions. In this example, the simultaneous calculation includes calculation of Young's moduli, Poisson's ratios and shear modulus in the orthogonal first and second in-plane directions. In an even more specific example in which the transducers are positioned along respective ones of 0°, 45° and 90° in-plane directions, the velocities of the acoustic waves detected by the transducers may include longitudinal wave velocities $V_L(0)$, $V_L(90)$ and $V_L(45)$, and transverse wave velocity $V_T(0)$. In this example, the simultaneous calculation of Young's moduli, Poisson's ratios and shear modulus may include solving the set of equations (14)-(18), as provided above.

Figure 3:
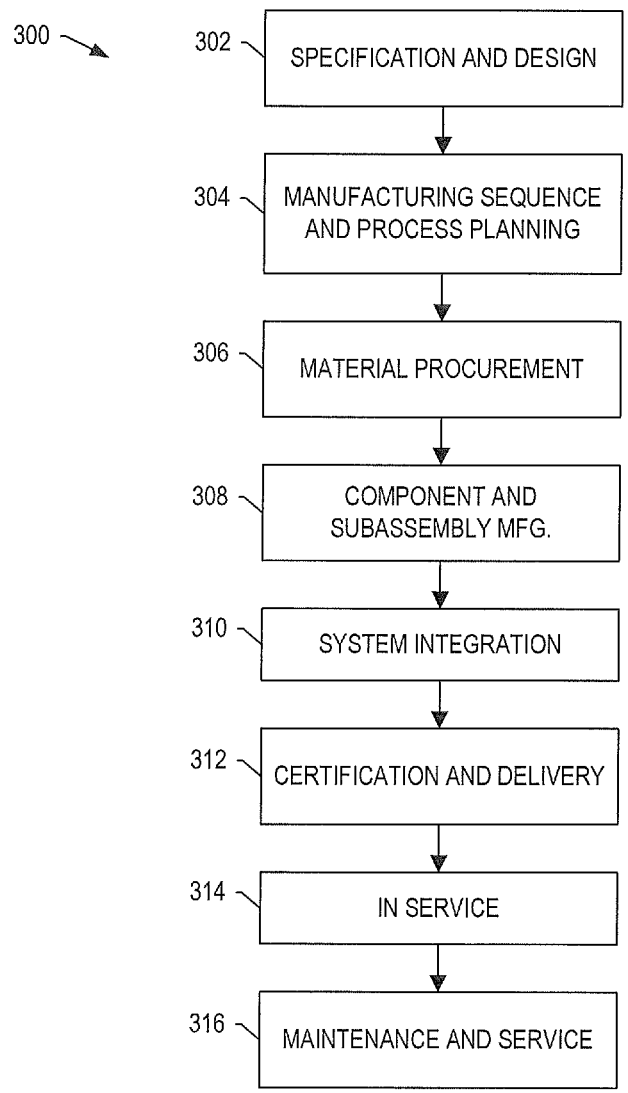
FIG. 3 is flowchart illustrating various operations in an aircraft production and service methodology according to one example implementation.
Figure 4:
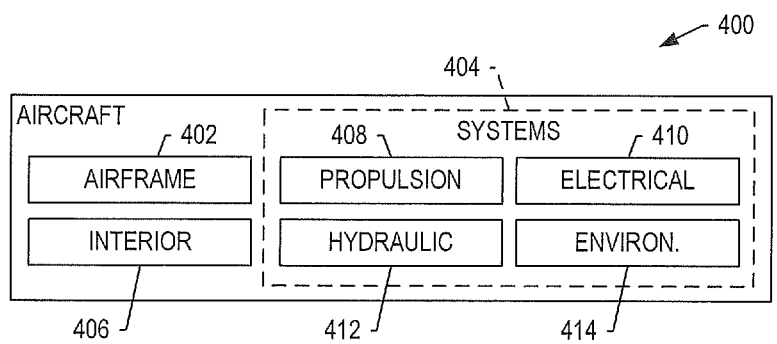
FIG. 4 is a block diagram of an aircraft according to one example implementation.

Example implementations of the disclosure may find use in a variety of potential applications, particularly in the transportation industry, including for example, aerospace, marine and automotive applications. Thus, referring now to FIGS. 3 and 4, example implementations may be used in the context of an aircraft manufacturing and service method 300 as shown in FIG. 3, and an aircraft 400 as shown in FIG. 4. During pre-production, the example method may include specification and design 302 of the aircraft, manufacturing sequence and processing planning 304 and material procurement 306. The disclosed method may be specified for use during the specification and design of the aircraft, and/or manufacturing sequence and process planning. During production, component and subassembly manufacturing 308 and system integration 310 of the aircraft takes place.

In various examples, portions of the aircraft may include laminates, and the disclosed apparatus and method may be used to measure in-plane elastic constants of one or more of these laminates during either or both of the component and subassembly manufacturing process 308 or system integration 310. Thereafter, the aircraft 400 may go through certification and delivery 312 in order to be placed in service 314. While in service by a customer, the aircraft may be scheduled for routine maintenance and service 316 (which may also include modification, reconfiguration, refurbishment or the like). The in-plane elastic constants of one or more laminates on the aircraft may be measured according to the disclosed apparatus method while in service, and in one example, during the maintenance and service.

Each of the processes of the example method 300 may be performed or carried out by a system integrator, third party and/or operator (e.g., customer). For the purposes of this description, a system integrator may include for example any number of aircraft manufacturers and major-system subcontractors; a third party may include for example any number of vendors, subcontractors and suppliers; and an operator may include for example an airline, leasing company, military entity, service organization or the like.

As shown in FIG. 4, an example aircraft 400 produced by the example method 300 may include an airframe 402 with a plurality of systems 404 and an interior 406. Laminates for which elastic constants may be measured according to the disclosed apparatus and method may be used in the airframe and/or within the interior. Examples of high-level systems 404 include one or more of a propulsion system 408, electrical system 410, hydraulic system 412, environmental system 414 or the like. Any number of other systems 404 may be included. Although an aerospace example is shown, the principles of the disclosure may be applied to other industries, such as the marine and automotive industries.

Systems and methods embodied herein may be employed during any one or more of the stages of the example production and service method 300. For example, components or subassemblies corresponding to production process 308 may include one or more laminates for which elastic constants may be measured according to the disclosed method while the aircraft 400 is in service 314. Also, one or more example system implementations, method implementations or a combination thereof may be utilized to measure elastic constants for one or more laminates during the production stages 308 and 310, which may in one example permit the identification of any changes in material properties that may be indicative of improper manufacture or degradation of the part. This may in turn substantially expedite assembly of or reduce the cost of an aircraft 400. Similarly, one or more of system implementations, method implementations or a combination thereof may be utilized while the aircraft 400 is in service 314, for example.

Many modifications and other implementations of the disclosure set forth herein will come to mind to one skilled in the art to which these disclosure pertain having the benefit of the teachings presented in the foregoing descriptions and the associated drawings. Therefore, it is to be understood that the disclosure are not to be limited to the specific implementations disclosed and that modifications and other implementations are intended to be included within the scope of the appended claims. Moreover, although the foregoing descriptions and the associated drawings describe example implementations in the context of certain example combinations of elements and/or functions, it should be appreciated that different combinations of elements and/or functions may be provided by alternative implementations without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. An apparatus comprising:
   an acoustic wave generator configured to simultaneously generate a plurality of acoustic waves that propagate through a laminate along a plurality of in-plane directions;
   a plurality of acoustic transducers spaced apart from one another and positionable at one or more known distances from the acoustic wave generator along respective in-plane directions, the acoustic transducers being configured to detect acoustic waves propagating through the laminate along the respective in-plane directions; and a processing device coupled to the acoustic transducers and configured to simultaneously calculate a plurality of elastic constants of the laminate as a function of velocities of the acoustic waves detected by the acoustic transducers, the processing device being configured to calculate the velocities as a function of the one or more known distances and arrival times of the acoustic waves at the acoustic transducers.

2. The apparatus of claim 1, wherein the acoustic wave generator comprises a target inducible to generate ultrasonic waves by an energy source configured to direct a pulse onto the target.

3. The apparatus of claim 1, wherein the acoustic transducers are positionable along respective ones of 0°, 45° and 90° in-plane directions.

4. The apparatus of claim 3 further comprising:
a support arm to which the acoustic transducers are affixed spaced apart from one another, the support arm being positionable to thereby position the acoustic transducers along respective ones of the 0°, 45° and 90° in-plane directions.

5. The apparatus of claim 1, wherein the in-plane directions include orthogonal first and second in-plane directions, and
wherein the processing device being configured to simultaneously calculate the plurality of elastic constants includes being configured to calculate Young's moduli, Poisson's ratios and shear modulus in the orthogonal first and second in-plane directions.

6. The apparatus of claim 5, wherein the acoustic transducers are positionable along respective ones of 0°, 45° and 90° in-plane directions, the velocities of the acoustic waves detected by the acoustic transducers including longitudinal wave velocities in the 0°, 45° and 90° in-plane directions, and a transverse wave velocity in the 0° in-plane direction, and
wherein the processing device is configured to simultaneously calculate the Young's moduli, Poisson's ratios and shear modulus based on the longitudinal wave velocities in the 0°, 45° and 90° in-plane directions, the transverse wave velocity in the 0° in-plane direction, and a known density of the laminate.

7. A method comprising:
simultaneously generating, by an acoustic wave generator, a plurality of acoustic waves that propagate through a laminate along a plurality of in-plane directions;
detecting, by a plurality of acoustic transducers, acoustic waves propagating through the laminate, the acoustic transducers being spaced apart from one another and positioned at one or more known distances from the acoustic wave generator along respective in-plane directions, the acoustic transducers being configured to detect acoustic waves propagating through the laminate along the respective in-plane directions; and
simultaneously calculating a plurality of elastic constants of the laminate as a function of velocities of the acoustic waves detected by the acoustic transducers, the velocities being calculated as a function of the one or more known distances and arrival times of the acoustic waves at the acoustic transducers.

8. The method of claim 7, wherein the acoustic wave generator comprises a target, and simultaneously generating the plurality of acoustic waves includes an energy source directing a pulse onto the target to thereby induce the target to generate ultrasonic waves.

9. The method of claim 7 further comprising:
disposing the acoustic wave generator and acoustic transducers against a major surface of the laminate so as to be in acoustical communication with the laminate.

10. The method of claim 7 further comprising:
disposing the acoustic wave generator and acoustic transducers against a portion of an aircraft that includes the laminate.

11. The method of claim 7, wherein the acoustic transducers are positioned along respective ones of 0°, 45° and 90° in-plane directions.

12. The method of claim 11, wherein the apparatus further comprises a support arm to which the acoustic transducers are affixed spaced apart from one another, the support arm being positioned to thereby position the acoustic transducers along respective ones of the 0°, 45° and 90° in-plane directions.

13. The method of claim 7, wherein the in-plane directions include orthogonal first and second in-plane directions, and
wherein simultaneously calculating the plurality of elastic constants includes calculating Young's moduli, Poisson's ratios and shear modulus in the orthogonal first and second in-plane directions.

14. The method of claim 13, wherein the acoustic transducers are positioned along respective ones of 0°, 45° and 90° in-plane directions, the velocities of the acoustic waves detected by the acoustic transducers including longitudinal wave velocities in the 0°, 45° and 90° in-plane directions, and a transverse wave velocity in the 0° in-plane direction, and
wherein the Young's moduli, Poisson's ratios and shear modulus are simultaneously calculated based on the longitudinal wave velocities in the 0°, 45° and 90° in-plane directions, the transverse wave velocity in the 0° in-plane direction, and a known density of the laminate.

15. A processing device comprising a processor and a memory storing computer-readable program code portions that, in response to execution by the processor, cause the processing device to at least:
determine arrival times of acoustic waves at a plurality of acoustic transducers of an apparatus that includes an acoustic wave generator and the acoustic transducers,
wherein the acoustic wave generator is configured to simultaneously generate a plurality of acoustic waves that propagate through a laminate along a plurality of in-plane directions, and
wherein the acoustic transducers are spaced apart from one another and positionable at one or more known distances from the acoustic wave generator along respective in-plane directions, the acoustic transducers being configured to detect acoustic waves propagating through the laminate along the respective in-plane directions, the arrival times being determined for the acoustic waves detected by the acoustic transducers; and
simultaneously calculating a plurality of elastic constants of the laminate as a function of velocities of the acoustic waves detected by the acoustic transducers, the velocities being calculated as a function of the one or more known distances and arrival times of the acoustic waves at the acoustic transducers.

16. The processing device of claim 15, wherein the acoustic wave generator comprises a target inducible to generate ultrasonic waves by an energy source configured to direct a pulse onto the target.

17. The processing device of claim 15, wherein the acoustic transducers are positionable along respective ones of 0°, 45° and 90° in-plane directions.

18. The processing device of claim 17, wherein the apparatus further comprises a support arm to which the acoustic transducers are affixed spaced apart from one another, the support arm being positionable to thereby position the acoustic transducers along respective ones of the 0°, 45° and 90° in-plane directions.

19. The processing device of claim 15, wherein the in-plane directions include orthogonal first and second in-plane directions, and
wherein the processing device being caused to simultaneously calculate the plurality of elastic constants includes being caused to calculate Young's moduli, Poisson's ratios and shear modulus in the orthogonal first and second in-plane directions.

20. The processing device of claim 19, wherein the acoustic transducers are positionable along respective ones of 0°, 45° and 90° in-plane directions, the velocities of the acoustic waves detected by the acoustic transducers including longitudinal wave velocities in the 0°, 45° and 90° in-plane directions, and a transverse wave velocity in the 0° in-plane direction, and
wherein the processing device is caused to simultaneously calculate the Young's moduli, Poisson's ratios and shear modulus based on the longitudinal wave velocities in the 0°, 45° and 90° in-plane directions, the transverse wave velocity in the 0° in-plane direction, and a known density of the laminate.

* * * * *